United States Patent
Burns

(10) Patent No.: US 9,220,623 B2
(45) Date of Patent: Dec. 29, 2015

(54) KNEE REHABILITATION EXERCISE DEVICE

(76) Inventor: Jebodiah Mose Burns, San Jose, CA (US)

(*) Notice: Subject to any disclaimer, the term of this patent is extended or adjusted under 35 U.S.C. 154(b) by 587 days.

(21) Appl. No.: 12/799,456

(22) Filed: Apr. 26, 2010

(65) Prior Publication Data
US 2011/0207585 A1    Aug. 25, 2011

Related U.S. Application Data

(63) Continuation-in-part of application No. 12/157,767, filed on Jun. 13, 2008, now abandoned.

(51) Int. Cl.
| | | |
|---|---|---|
| *A61F 5/04* | (2006.01) | |
| *A61F 5/042* | (2006.01) | |
| *A63B 21/055* | (2006.01) | |
| *A63B 21/16* | (2006.01) | |
| *A63B 23/035* | (2006.01) | |
| *A61F 5/01* | (2006.01) | |
| *A63B 23/04* | (2006.01) | |
| *A63B 21/00* | (2006.01) | |
| *A63B 21/04* | (2006.01) | |
| *A63B 22/00* | (2006.01) | |

(52) U.S. Cl.
CPC ........... *A61F 5/0123* (2013.01); *A63B 21/0004* (2013.01); *A63B 21/0552* (2013.01); *A63B 21/1426* (2013.01); *A63B 21/1449* (2013.01); *A63B 23/0405* (2013.01); *A63B 23/0494* (2013.01); *A61F 2005/0137* (2013.01); *A61F 2005/0179* (2013.01); *A63B 21/0421* (2013.01); *A63B 21/0442* (2013.01); *A63B 21/0557* (2013.01); *A63B 2022/0094* (2013.01)

(58) Field of Classification Search
CPC .. A63B 21/02; A63B 21/055; A63B 21/0552; A63B 21/0421; A63B 21/0407; A63B 23/04; A63B 23/0405; A63B 23/0494; A63B 21/0004; A63B 21/0442; A63B 21/0557; A63B 21/1426; A63B 21/1449; A63B 2022/0094; A61F 5/04; A61F 5/042; A61F 5/0123; A61F 2005/0137; A61F 2005/0179
USPC ................ 602/5, 16, 23, 26–27; 482/79, 105, 482/121–122, 124
See application file for complete search history.

(56) References Cited

U.S. PATENT DOCUMENTS

| | | | | |
|---|---|---|---|---|
| 4,606,542 | A * | 8/1986 | Segal | 482/124 |
| 5,203,754 | A * | 4/1993 | Maclean | 482/124 |
| 5,213,094 | A * | 5/1993 | Bonutti | 601/33 |
| 6,117,097 | A * | 9/2000 | Ruiz | 602/26 |
| 7,261,679 | B2 * | 8/2007 | Sload | 482/124 |
| 8,376,918 | B2 * | 2/2013 | Itzkowitz | 482/121 |

* cited by examiner

*Primary Examiner* — Alireza Nia
*Assistant Examiner* — Camtu Nguyen
(74) *Attorney, Agent, or Firm* — Klarquist Sparkman, LLP

(57) ABSTRACT

A knee rehabilitation exercise device comprised of a right and left leg brace, a rear knee strap, an upper leg strap assembly, a lower leg strap assembly, a portable rear brace assembly and an elastic resistance band. The left and right leg brace members are each comprised of an upper member and a lower member rotatably pinned together at the area of the knee joint. The left and right leg braces are attached to the upper and lower leg strap assembly. The rear knee strap is attached to the left and right leg braces at the knee joint. When a user places the elastic resistance band onto L hooks mounted on the upper and lower strap assembly, and the rear brace assembly is placed between the rear of the user's knee and the elastic resistance band, a resistive stretching is caused when the user straightens his leg which exercises and strengthens the user's leg muscles in the area of the knee joint.

10 Claims, 16 Drawing Sheets

KNEE REHABILITATION EXERCISE DEVICE

CROSS REFERENCE TO RELATED APPLICATIONS APPLICATION

This is a continuation-in-part of application Ser. No. 12/157,767, filed Jun. 13, 2008, now abandoned.

BACKGROUND OF THE INVENTION

This invention relates generally to the field of portable leg exercise devices and more specifically to a knee rehabilitation exercise device.

With today's rigorous sports activities including football, tennis, basketball and soccer it is unfortunately a common occurrence for active people to injure there knee joint to the point where surgical treatment is necessary to repair the knee and areas around the knee.

Because of this, it has been necessary to provide devices to help rehabilitate the knee area after surgery. Some devices are simply leg braces that help take pressure off the knee joint while it is healing. Other devices are machines or apparatus that help strengthen the leg muscles around the knee and associated with proper knee function.

Patents that describe leg braces that help keep the knee joint supported during exercise include U.S. Pat. Nos. 4,982,732, 5,116,296, 4,433,679 and 5,980,435. Patents that describe exercise apparatus for helping to rehabilitate the muscles of the leg around the knee joint include U.S. Pat. Nos. 4,546,968, 4,776,587, 4,979,737 and 5,181,895. However, these patents and other commercially available exercise devices have a deficiency in that none of them allows a person to wear a light weight inexpensive brace which has hooks attached to allow the user to releasably attach an elastic band from the area of the upper leg to the area of the lower leg, and to insert a portable assembly behind the user's knee for the elastic band to stretch over to increase the resistance factor to the muscles surrounding the knee joint. Furthermore, none of the patents or other prior art shows a leg brace exercise device that allows the user to easily and quickly change the resistance band location from the back of the leg to the front of the leg whereby the user can insert a portable assembly in front of the knee which the elastic band passes over to passively stretch the knee joint to a straight position.

BRIEF SUMMARY OF THE INVENTION

The primary object of the invention is to provide a knee rehabilitation exercise device that allows a person to strengthen leg muscles after knee surgery.

Another object of the invention is to provide a knee rehabilitation exercise device that helps increase the range of knee joint motion.

Another object of the invention is to provide a knee rehabilitation exercise device that can be easily used by a person without the need for additional help from a caregiver.

A further object of the invention is to provide a knee rehabilitation exercise device that is lightweight and can be adjusted to fit a variety of leg lengths and diameters.

Yet another object of the invention is to provide a knee rehabilitation exercise device that can be fastened to a user's leg quickly and easily.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a knee rehabilitation exercise device comprising: a left rigid leg brace, a right rigid leg brace, a rear knee strap, an upper leg strap assembly, a lower leg strap assembly, a portable rear brace assembly, an elastic resistance band, said left and right leg brace members each comprised of an upper member and a lower member rotatably pinned together at the area of the knee joint, said left and right leg brace attached at their uppermost ends to said upper leg strap assembly, said left and right leg brace attached at their lowermost ends to said lower leg strap assembly, said upper leg strap assembly including a rear facing upwardly turned L hook, said lower leg strap assembly including a rear facing downwardly turned L hook, said upper and lower leg strap assemblies able to be formed into a circular shape by a user so that said upper leg strap assembly fits around said user's thigh and said lower leg strap assembly fits around the user's ankle, said upper and lower leg strap assemblies secured to said user's leg by standard snap fasteners, said rear knee strap fixedly held at said pinned knee joint by said left and right leg brace, said rear brace assembly held in place behind said user's knee joint by said elastic resistance band when said upper and lower L hooks interact with an upper and a lower aperture in said band, so that when said user straightens his knee from a bent position, said elastic band stretches putting pressure on said rear brace assembly, and said pressure transferring to said user's leg muscles causing them to contract and strengthen after repeated use.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 12 shows a portable brace assembly 200 that is designed to attach to a standard leg brace. The standard leg brace includes a pair of parallel vertically oriented stiff bar like members 210 connected by a pair of resilient horizontal members 205, 206. Each bar member 210 is pivotally hinged by pivot pins 212. A resilient leg wrap 220 is also part of the standard knee brace and wraps around the user's leg 222. Now, referring to the unique components of the portable brace assembly 200, an elastic member 202 is attached in four places 208, 209 to the leg brace. A knee pad 214 rests on the user's knee and a resistance post 216 is placed between the knee pad 214 and the elastic member 202. An extension post 204 protrudes through an aperture 238 in elastic member 202. A support disk shown by dotted line 236 helps support elastic member 202 and prevent it from falling toward the knee pad 214.

DETAILED DESCRIPTION OF THE PREFERRED EMBODIMENTS

Figure 1:
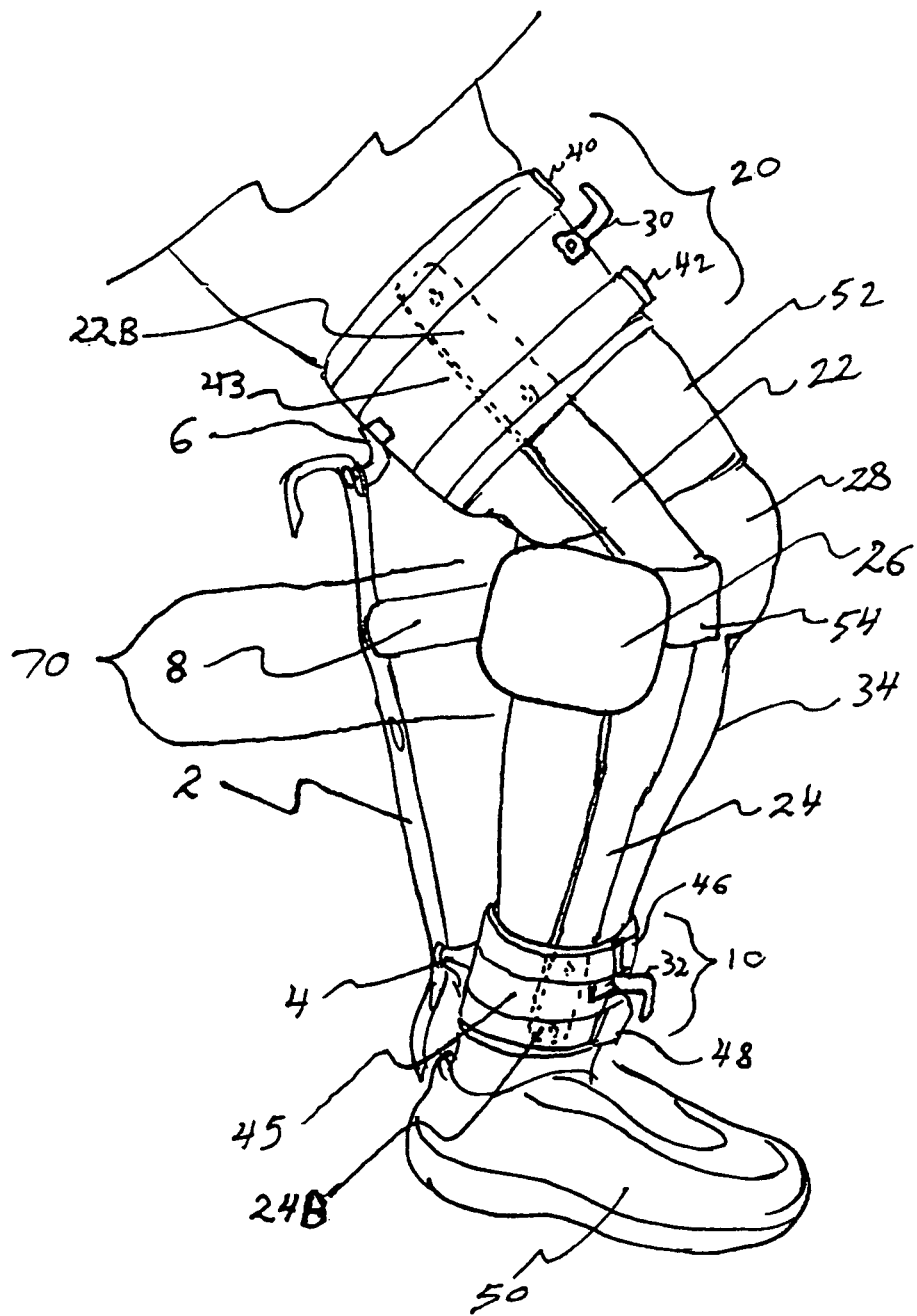
FIG. 1 is a perspective view of the invention with elastic stretch band in place and the knee in the bent position.
Figure 4:
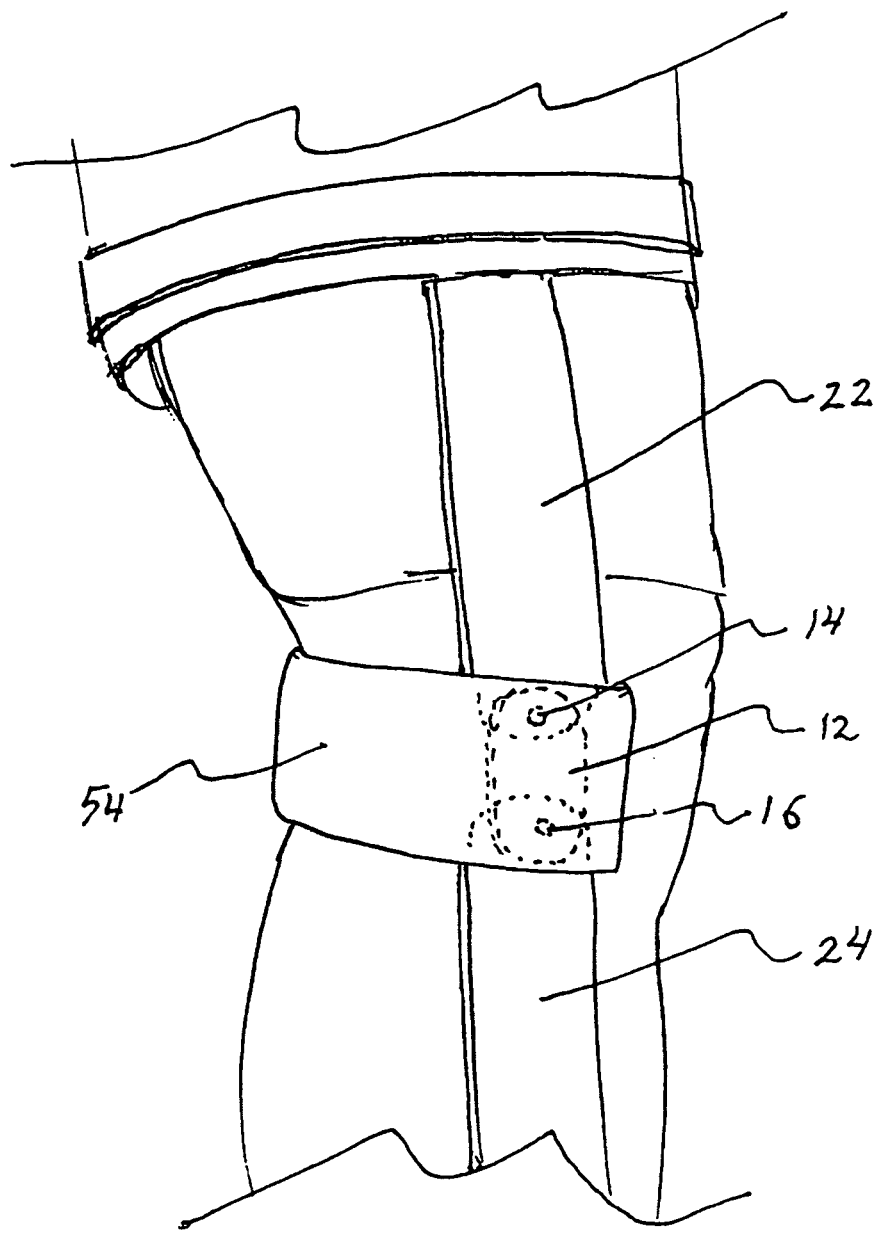
FIG. 4 is side view of the invention showing the rear knee strap.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner. Referring now to FIG. 1 we see a side view of a person's leg 34 and wearing the leg brace of the present invention. A top flexible leg strap assembly 20 is attached to a pair of rigid leg braces. Each leg brace is comprised of an upper half 22 and a lower half 24. Both left and right leg braces can be seen clearly in FIG. 11 and are shown as left brace 22, 24 and right brace 22A and 24A. The rigid leg brace members are pinned as shown by dotted lines 14, 16 in FIG. 4 to an intermediate plate 12 that connects upper brace member 22 to lower brace member 24 via rotatable pin joints 14, 16. FIG. 4 also clearly shows rear knee joint strap 54, which prevents the leg brace members 22, 24 from being pushed forward when under pressure from elastic band 2. Referring back to FIG. 1, leg brace portion 22 extends to the top of nylon leg strap 43 as shown by dotted line 22B and to the bottom of leg strap 45 as shown by dotted line 24B. The leg brace members 22, 24 are fixedly attached to the nylon leg straps 43, 45 so that they prevent the two leg strap assemblies 10, 20 from sliding towards the knee joint when resistive force is applied by elastic stretch band 2. Nylon strap 43 is approximately five inches wide and nylon strap 45 is approximately four inches wide.

Figure 2:
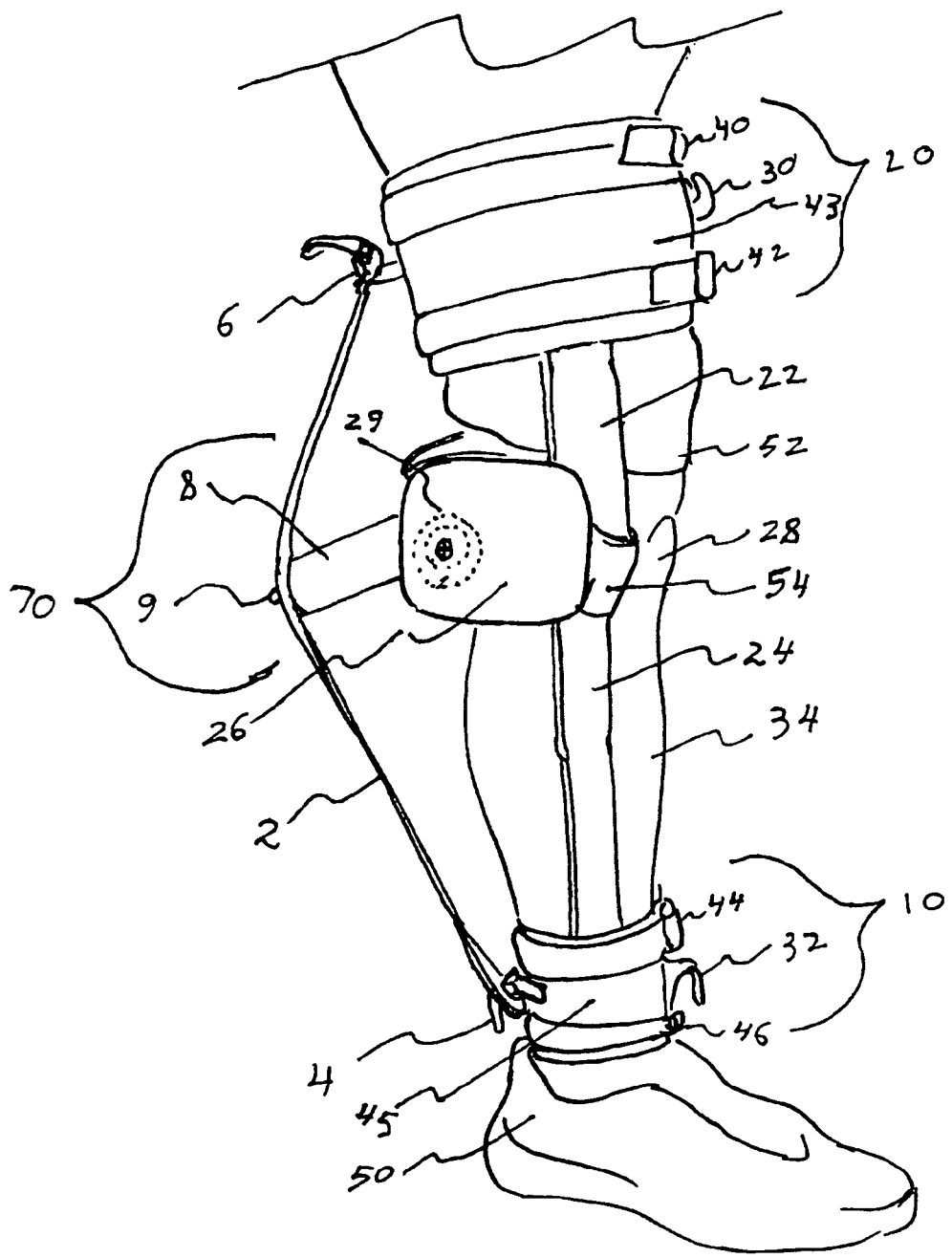
FIG. 2 is a perspective view of the invention with the elastic stretch band in place and the knee in the straightened position.

Elastic stretch band 2 is attached to L hook 6 on the upper leg strap 43 and L hook 4 on the lower leg strap 45. Rear leg brace assembly 70 is portable and can be placed between the elastic stretch band 2 and the rear of the user's knee 28 where rear knee strap 54 is located. The outwardly facing horizontal post 8 of portable brace assembly 70 engages elastic stretch band 2 so that when the user straightens his or her leg 34, as shown in FIG. 2, the elastic stretch band 2 is stretched and thereby puts a resistive force on the users muscles associated with the knee joint, specifically the rectus femoris, vastus lateralis, intermedialis and vastus medialus oblique muscles. By repeated bending and straightening of the knee joint, the user can help rehabilitate the muscles associated with the knee joint after knee surgery. The present invention can also be used as a leg strengthening exercise for non-surgical conditions to keep the muscles around the knee in top shape. The exercise can be done by an individual without the help of an assistant. The rigid leg braces 22, 24 are preferably made of aluminum and the leg straps 43, 45 are made of plastic sheet nylon type six, approximately one sixteenth of an inch thick, so the entire assembly is light weight. The nylon straps 43, 45 have enough flexibility to be able to adjust to a person's thigh and ankle, but are also rigid enough that they will not deform when resistive pressure is applied by elastic stretch band 2.

Figure 3:
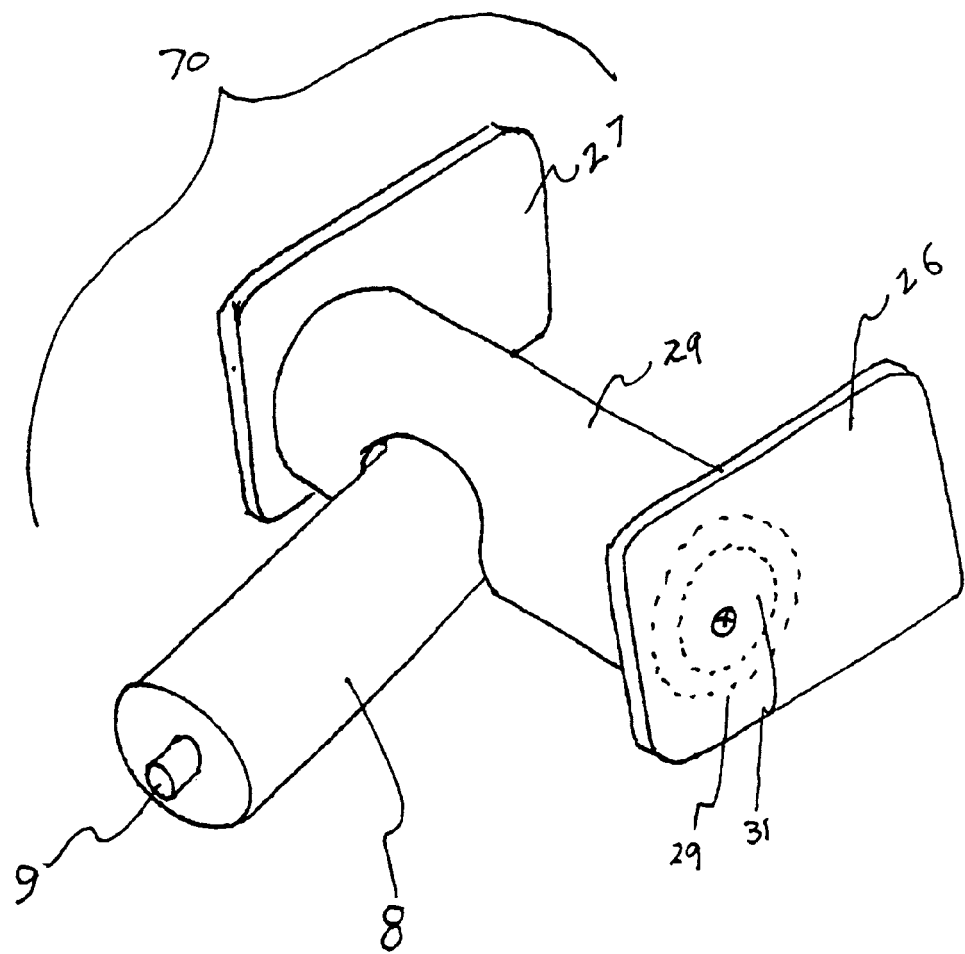
FIG. 3 is a perspective view of the portable rear strengthening assembly.

Side plates 26, 27 on portable knee brace assembly 70 help keep the knee from slipping off cross bar 29 as shown in FIG. 3. Crossbar 29 is comprised of a padded layer as shown by dotted line 29 and a solid rod portion as shown by dotted line 31. Extension post 9 engages and protrudes through an aperture 2A in elastic stretch band 2 thereby holding the post 8 in place.

Figure 5:
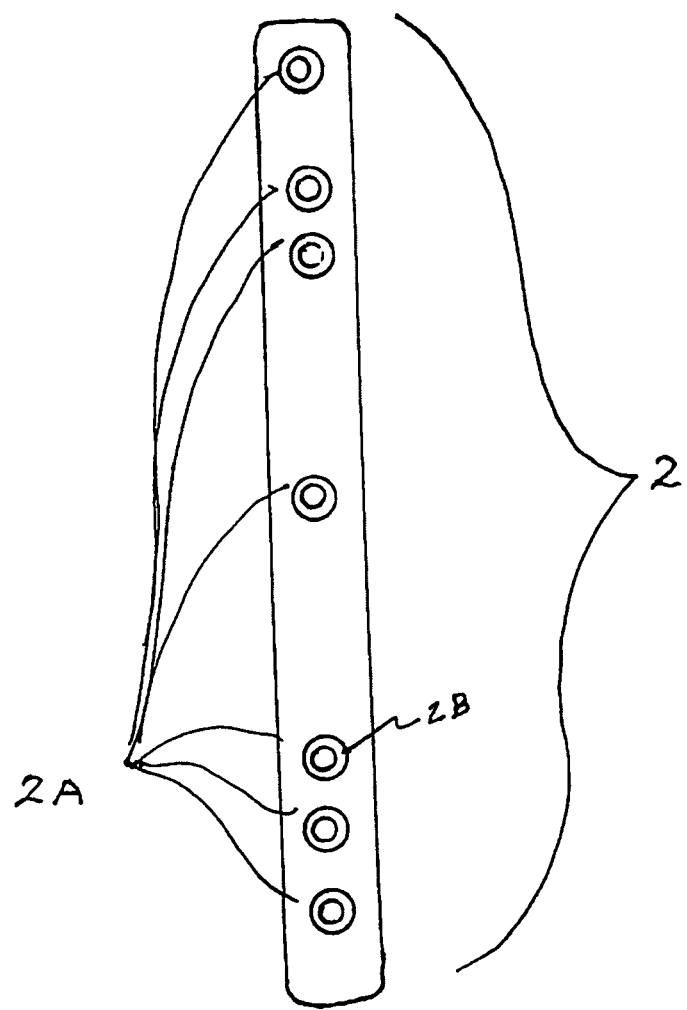
FIG. 5 is a plan view of the elastic stretch band.

Elastic stretch band 2 is shown clearly in FIG. 5. A series of apertures 2A are each reinforced by a standard metal or plastic grommet 2B. The elastic stretch band is made of highly elastic material such as latex rubber. The elastic stretch band can be made in a variety of thicknesses to provide varying degrees of resistance. Additionally, the user can adjust the length of the elastic stretch band 2 by choosing which aperture 2A to use to engage L hooks 4, 6. The shorter the distance of the elastic stretch band, the more resistance is applied to the user's leg muscles. Because the elastic stretch band can be easily removed and replaced, the user always has the option to increase or decrease resistive force by adjusting the elastic stretch band length or by replacing one elastic stretch band with another thinner or thicker one. Another method of applying resistive force, in place of the elastic stretch band 2, is to incorporate a torsion spring at the joint location of the leg brace. The torsion spring would perform the same effect as the elastic stretch band, however, my experiments have shown that the elastic stretch band is preferable because is provides a smoother range of resistance and can be easily replaced by other more or less elastic stretch bands.

Figure 6:
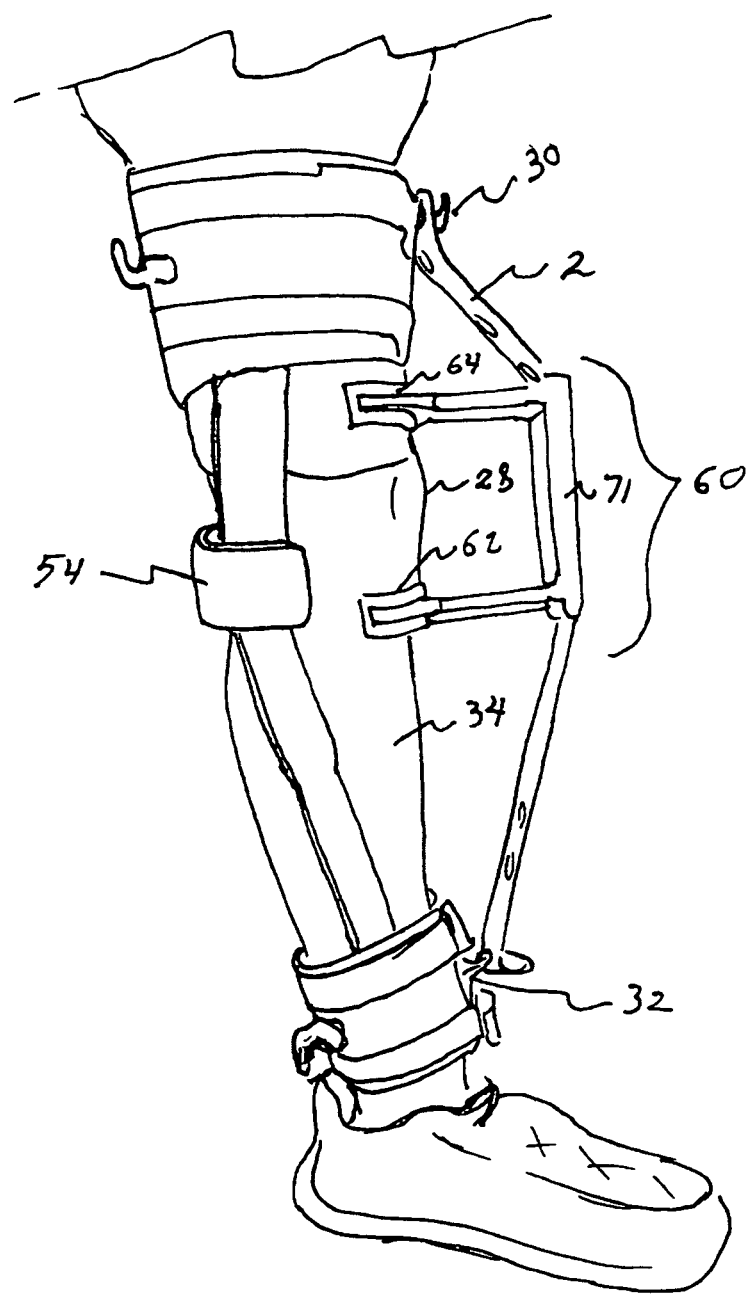
FIG. 6 is a lateral perspective view of the invention with the elastic stretch band in place.
Figure 8:
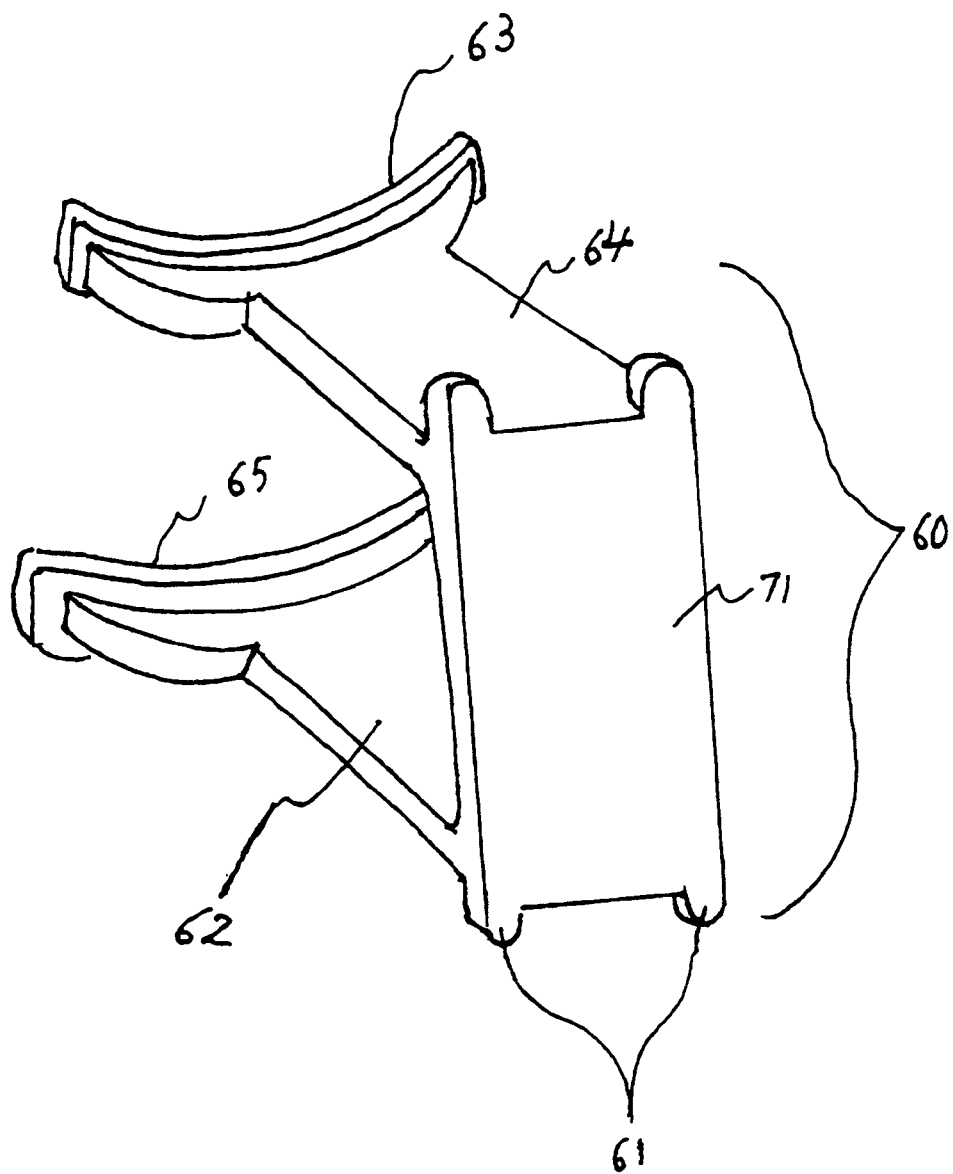
FIG. 8 is a perspective view of the portable front brace assembly.

FIG. 6 shows a side view of the invention where the user has attached the elastic stretch band to the front downward facing and front-upward facing L hooks 30, 32 and incorporated portable front stretch assembly 60 to provide a passive stretching of the knee joint to help straighten a person's leg after knee surgery. It is common for a person to have a difficult time making his or her leg straight after knee surgery. This configuration of the invention helps the muscles and knee joint stretch into an extended position. It is an important and novel feature of the present invention that one device can perform both functions of providing resistance to muscles around the knee when used in one mode and providing a stretching of the muscles and knee joint when used in the second mode. FIG. 8 shows a clear view of the portable front stretch assembly 60. It is comprised of a top and bottom horizontal plate 64, 62 and a vertical plate 71. The vertical plate has tabs 61 at each corner to help retain the elastic stretch band 2. The spacing of the top plate 64 and the bottom plate 62 is such that the user's knee 28 is spared from any contact, which would be uncomfortable after knee surgery. Padded members 63, 65 interact with the users leg just above and below the knee and provide comfort when the resistive force is applied by elastic stretch band 2.

Figure 7:
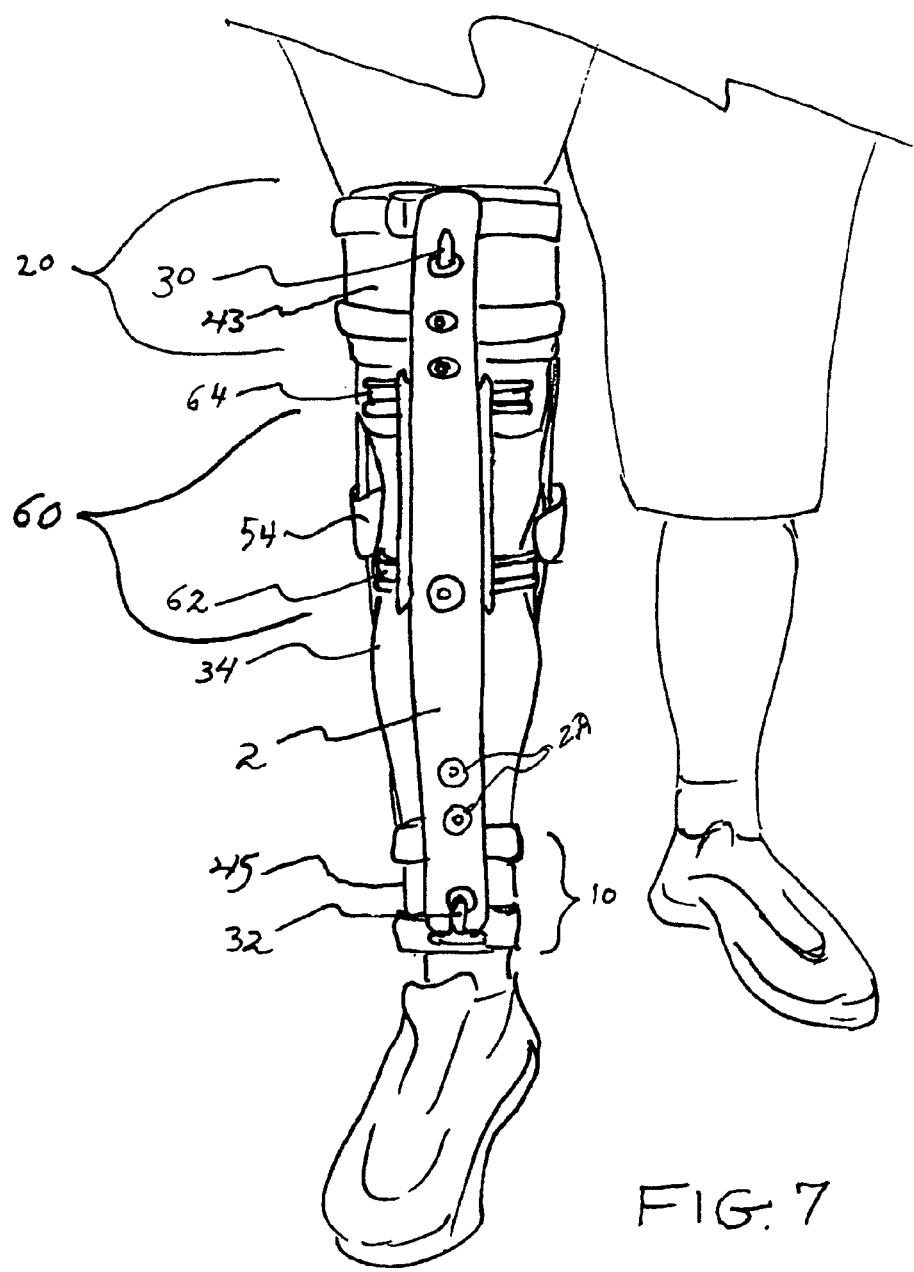
FIG. 7 is a front perspective view of the invention with the elastic stretch band in place.

FIG. 7 shows a front view of the front brace assembly in operation. The user can increase the stretching and straightening of the leg by disengaging apertures 2A and engaging apertures that would make the working length of the elastic stretch band 2 shorter.

Figure 9:
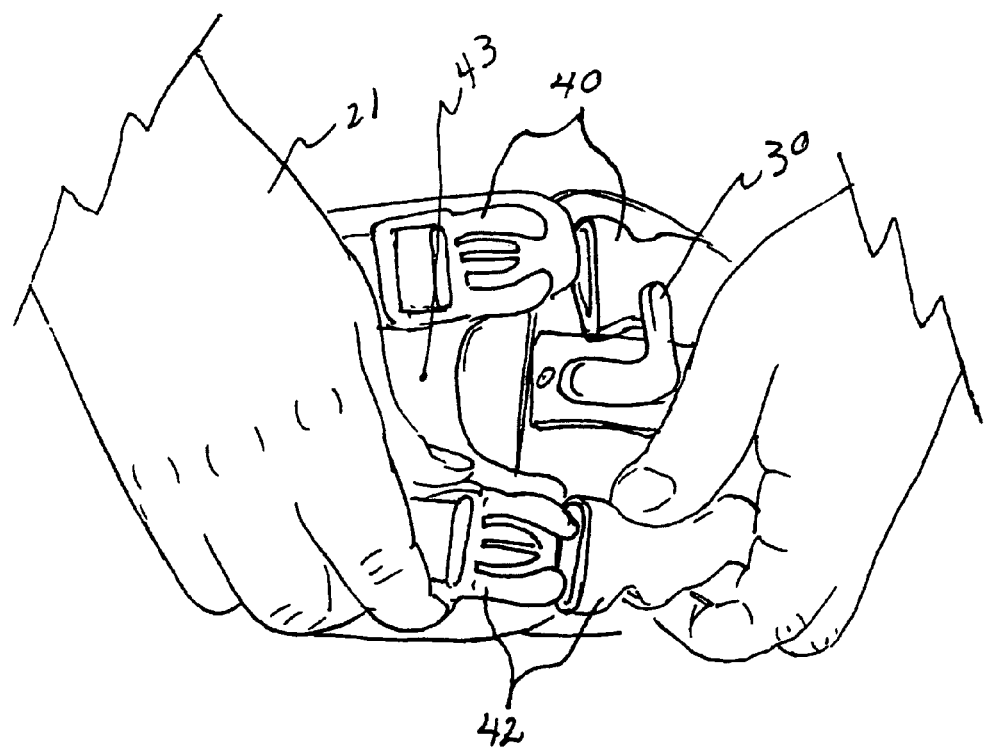
Figure 10:
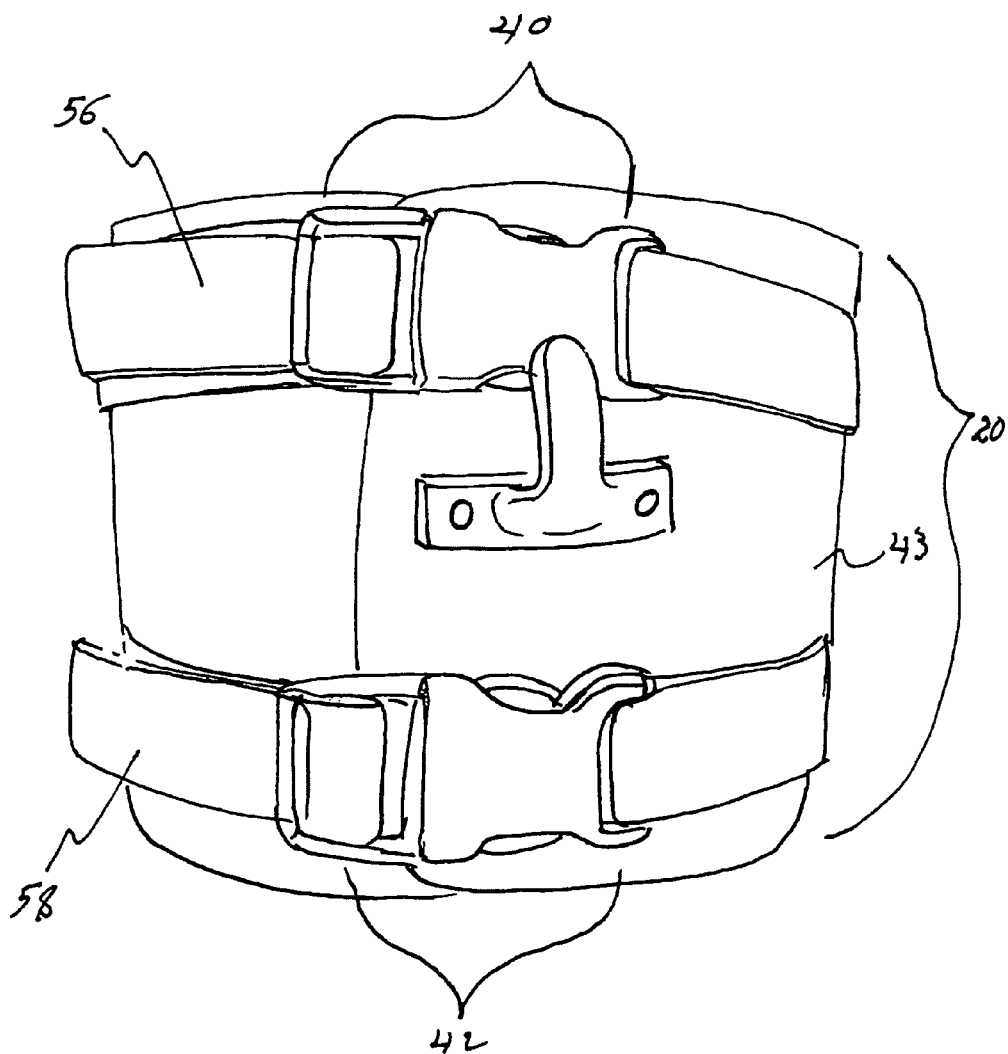
Figure 11:
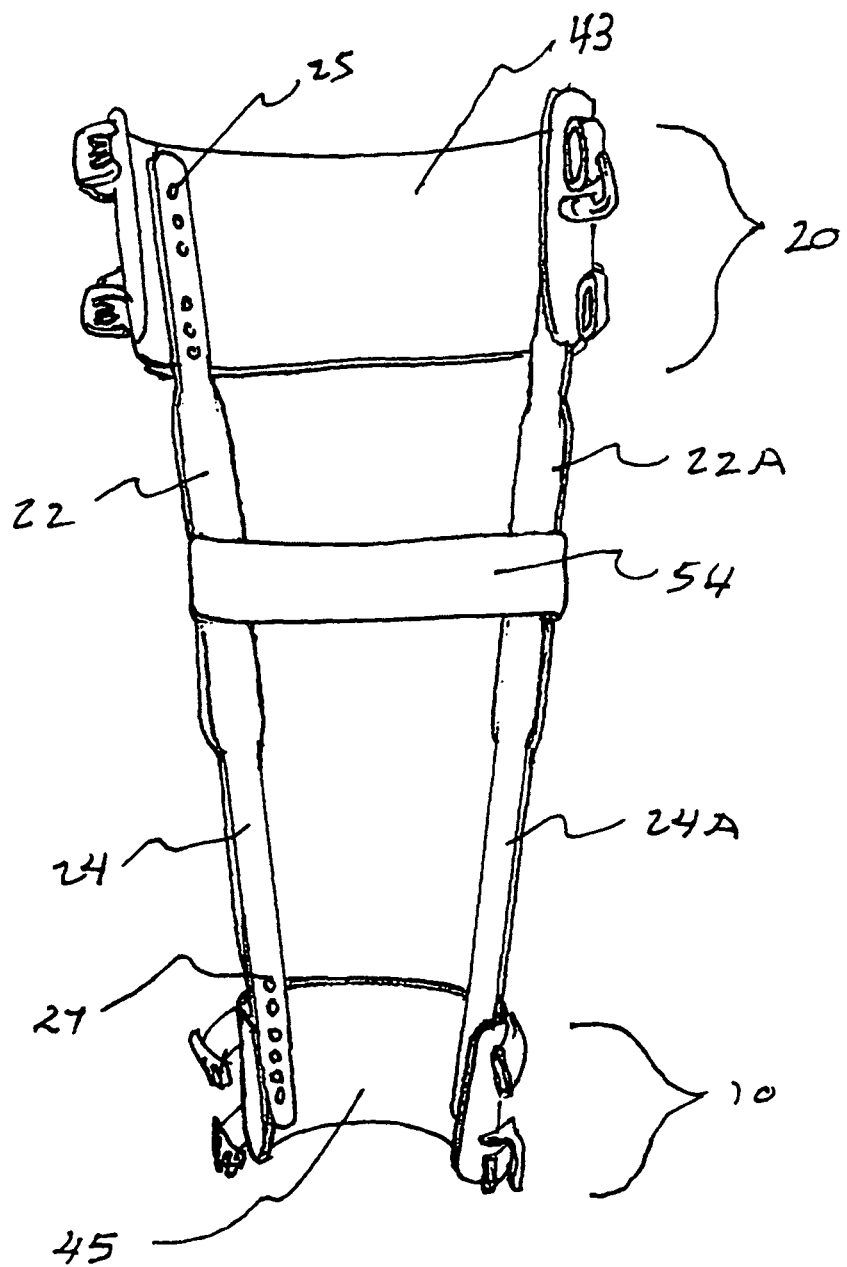
FIG. 11 is a perspective view of the leg strap and brace assembly.

FIG. 9 shows a user 21 connecting one side of the nylon leg strap 43 with the other forming a circular pattern around the user's thigh. The attachment buckles 40, 42 are standard snap fasteners. They are attached to polyester straps 56, 58 that are fixedly attached to the nylon strap 43 as shown in FIG. 11, which shows the snaps 40, 42 in their closed position. The loose ends of polyester straps 56, 58 can be pulled by the user to tighten the nylon leg strap 43 around the user's thigh. The same holds true for lower leg strap assembly 10 where nylon strap 45 is tightened around the user's ankle by closure snaps 46 and 48 and tightened in a similar way as upper leg strap assembly 20.

FIG. 11 shows the leg brace assembly in its open, ready to use position. Multiple apertures 25 in the rigid brace 22 allow the user to adjust the height of nylon strap 43, which is attached to brace 22 by standard fasteners that extend through both the strap 43 and the brace 22. The same holds true for lower leg strap 45 where apertures 27 allow the user to adjust the height of the strap 45 thereby allowing a person to adjust the entire device to the user's leg length.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

Figure 12:
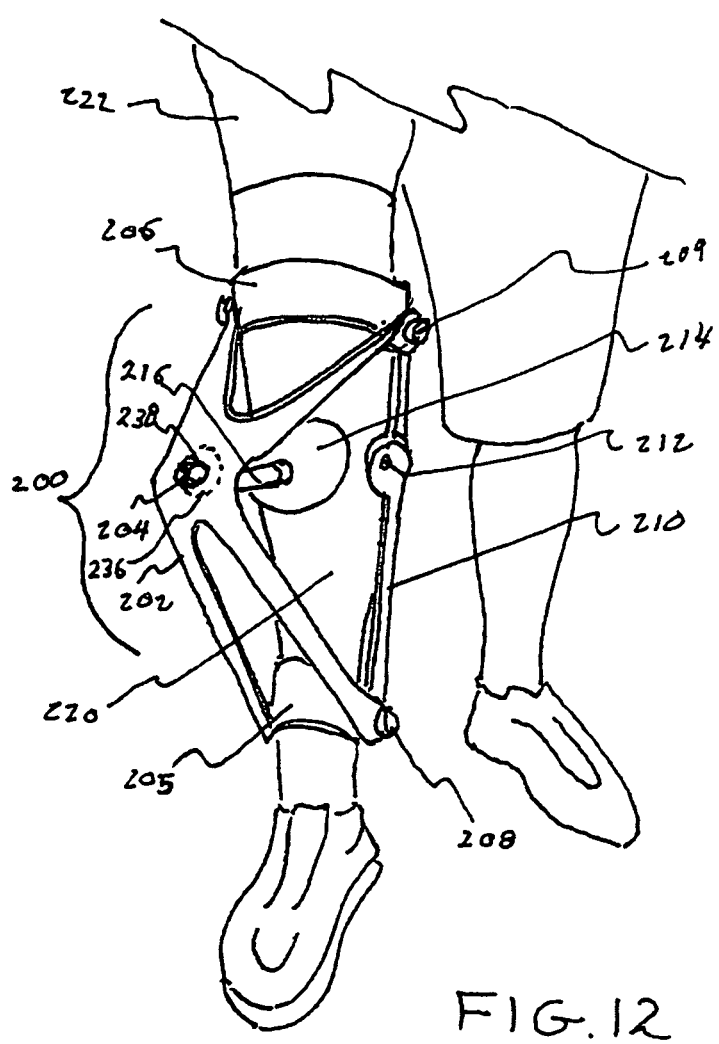
FIG. 12 is a perspective view of an alternate embodiment of the invention that attaches to a standard leg brace.

FIG. 12 shows an alternate embodiment of the invention 200 that is designed to attach to a standard leg brace. The standard leg brace includes a pair of parallel vertically oriented stiff bar like members 210 connected by a pair of resilient horizontal members 205, 206. Each bar member 210 is pivotably hinged by pivot pins 212. A resilient leg wrap 220 is also part of the standard knee brace and wraps around the user's leg 222. Now, referring to the unique components of the alternate embodiment 200, an elastic member 202 is attached in four places 208, 209 to the leg brace. A knee pad 214 rests on the user's knee and an outer tubular member 216 is placed between the knee pad 214 and the elastic member 202. A support disk shown by dotted line 236 helps support elastic member 202 and prevent it from falling toward the knee pad 214.

Figure 13:
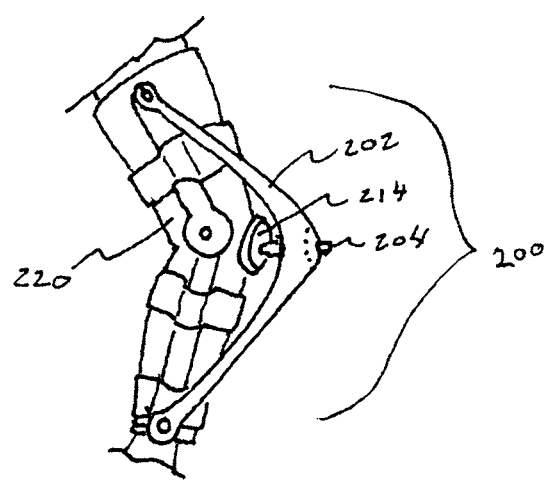
FIG. 13 shows a side view of the portable brace assembly 200. When the user relaxes his leg, the elastic member 202 shortens, thereby causing the knee joint to be stretched into a passively extended position.

FIG. 13 shows a side view of the alternated embodiment 200. When the user relaxes his leg, the elastic member 202 shortens, thereby causing the knee joint to be stretched into a passively extended position.

Figure 14:
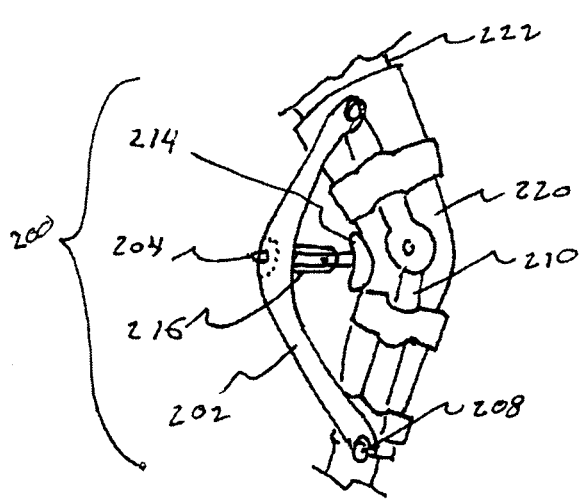
FIG. 14 shows the same portable brace assembly 200. However, the knee pad 214 has been turned around and the elastic member 202 is now at the rear of the user's leg. In this modality, the user can exercise his or her leg extension muscles while performing a leg extension exercise, during the process of going from a bent leg position to a straight leg position.

FIG. 14 shows the same alternate embodiment 200. However, the knee pad 214 has been turned around and the elastic member 202 is now at the rear of the user's leg. In this modality, the user can exercise his or her leg extension muscles while performing a leg extension exercise, during the process of going from a bent leg position to a straight leg position.

Figure 15:
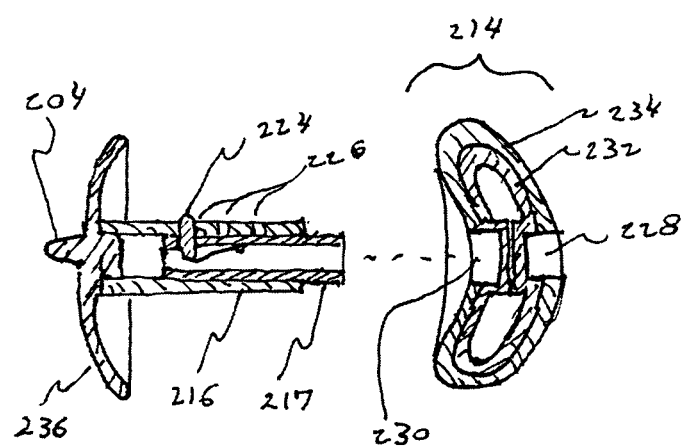
FIG. 15 is a side section view of the adjustable portion of the alternate embodiment.

FIG. 15 is a side view section that bisects the knee pad 214 and the extension post assembly which is comprised of an outer tubular member 216, an inner tubular member 217, an elastic support disk 236 and an extension post 204. The outer tubular member 216 can be slid up or down the inner tubular member 217 to adjust the overall length of the support 216, 217 thereby increasing or decreasing the amount of tension applied to elastic member 202. A spring biased pin 224 holds the two tubular members 216, 217 in place by engaging apertures 226. The knee pad assembly 214 is comprised of a rigid molded portion 232 and a resilient over molded portion 234. The center of both the concave side of the pad 214 and the convex side of the pad 214 include depressions that are sized to accept the end of inner tubular member 217, thereby holding the tube 217 in place while a leg exercise is being performed. The inner tube 217 is plugged into the concave portion of pad 214 via socket 230 when doing leg extension exercises and 217 is plugged into the convex socket 228 when doing a passive knee extension stretch.

Figure 16:
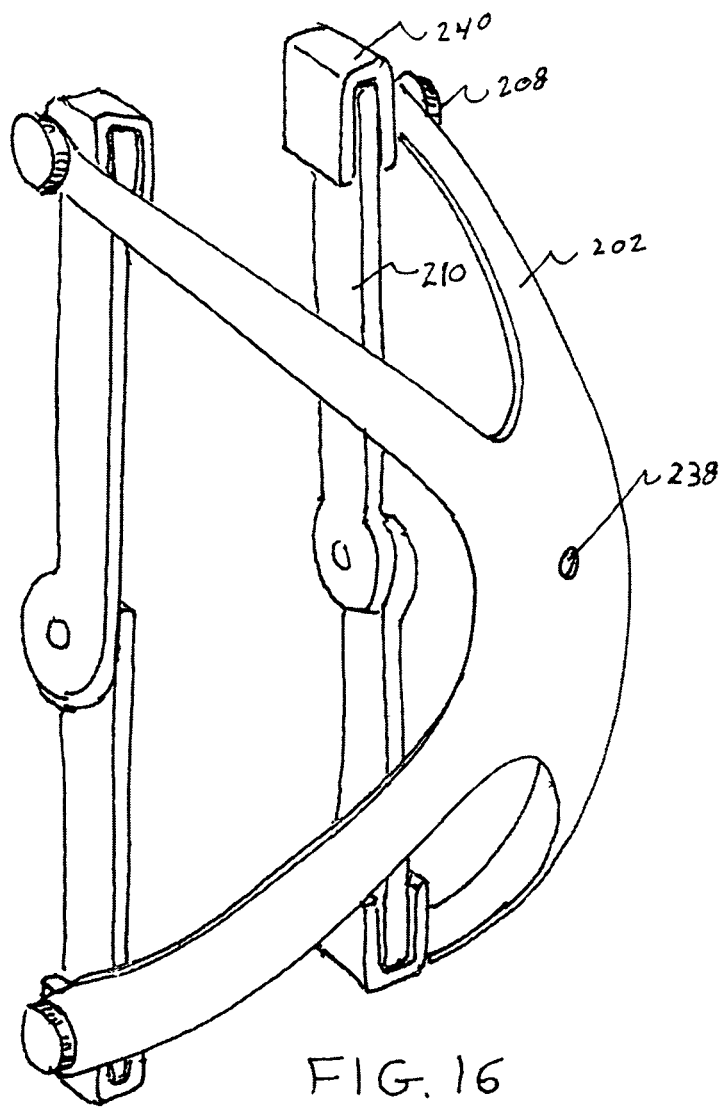
FIG. 16 is a perspective view of the alternate embodiment showing attachment means to a leg brace.

FIG. 16 shows a perspective view of the alternate embodiment elastic member 202. Aperture 238 can be clearly seen. Additionally, the method of attachment of elastic member 202 can be seen. U shaped channels 240 engage each end of the leg brace bars 210. A threaded aperture in each U shaped channel accepts a threaded bolt having a hand tightening knob 208 at its head. Each end of the elastic member 202 includes an aperture that allows the bolt of knob 208 to pass through so that when a user turns the knob 208 clockwise, the inner flat portion of the knob 208 traps the end of the elastic member 208 and prevents it from moving while exercising as described above.

What is claimed is:

1. Knee rehabilitation exercise device comprising:
    a left leg brace;
    a right leg brace;
    a rear knee strap;
    an upper leg strap assembly;
    a lower leg strap assembly;
    a portable rear brace assembly positioned to face the rear of a user's knee;
    an elastic stretch band;
    said left and right leg braces each comprised of a rigid upper member and a rigid lower member rotatably pinned together to provide a pinned knee joint at the area of said user's knee joint;
    said rigid upper member of each of said left and right leg braces being attached to said upper leg strap assembly;
    said rigid lower member of each of said left and right leg braces being attached to said lower leg strap assembly;
    an upper fastener attaching said elastic stretch band to said upper leg strap assembly;
    a lower fastener attaching said elastic stretch band to said lower leg strap assembly;
    said upper and lower leg strap assemblies being able to be formed into a circular shape by said user so that said upper leg strap assembly fits around said user's thigh and said lower nylon leg strap assembly fits around said user's ankle;
    said upper and lower leg strap assemblies being configured to releasably secure said exercising device to said user's leg;
    said rear knee strap being fixedly held at said pinned knee joint to said left and right leg braces;
    said portable rear brace assembly held in place behind said user's knee joint by said elastic stretch band;
    so that when said user straightens said user's knee from a bent position, said elastic stretch band stretches putting pressure on said portable rear brace assembly and
    said pressure transferring to said user's leg muscles causing them to contract and strengthen after repeated use.

2. Knee rehabilitation exercise device as claimed in claim 1 wherein:
    said upper fastener comprises a rear facing upwardly turned L hook on the upper leg strap assembly and an aperture defined in said elastic stretch band, which aperture receives said rear facing upwardly turned L hook to attach said elastic stretch band to said upper leg strap assembly; and said lower fastener comprises a rear facing downwardly turned L hook on the lower leg strap assembly and an aperture defined in said elastic stretch band, which aperture receives said rear facing downwardly turned L hook to attach said elastic stretch band to said lower leg strap assembly.

3. Knee rehabilitation exercise device as claimed in claim 1 wherein
said portable rear brace assembly is comprised of a padded first horizontal bar having left and right ends, a second horizontal bar centrally attached to said first horizontal bar and left and right knee retaining panels respectively fixedly attached to said left and right ends of said first horizontal bar;
said second horizontal bar terminates at its free end in an outwardly projecting post; and
said elastic stretch band defines an aperture that receives said post so that said first horizontal bar rests behind said user's knee joint and said second horizontal bar extends outward to engage said elastic stretch band causing said elastic stretch band to stretch and apply resistive pressure to said user's leg muscles.

4. Knee rehabilitation exercise device as claimed in claim 1 wherein said elastic stretch band in conjunction with said portable rear brace assembly provides resistance and strengthening to said user's rectus femoris, vastus lateralis, intermedialis and vastus medialis oblique muscles.

5. Knee rehabilitation exercise device as claimed in claim 1 wherein
said upper and lower leg strap assemblies are each comprised of a flexible sheet plastic nylon strap;
said upper leg strap assembly is approximately five inches wide and said lower leg strap assembly is approximately four inches wide;
said upper and lower leg strap assemblies are removably retained by polyester belting and snap fastening buckles attached to said belting.

6. Knee rehabilitation exercise device comprising:
a left leg brace;
a right leg brace;
an upper leg strap assembly;
a lower leg strap assembly;
a portable front brace assembly positioned to face the front of a user's knee, said portable front brace assembly having upper and lower padded portions shaped and positioned to engage said user's leg with said upper padded portion positioned above said user's knee and said lower padded portion positioned below said user's knee;
an elastic stretch band;
said left and right leg braces each comprised of a rigid upper member and a rigid lower member rotatably pinned together at the area of said user's knee joint;
said rigid upper member of each of said left and right leg braces being attached to said upper leg strap assembly;
said rigid lower member of each of said left and right leg braces being attached to said lower leg strap assembly;
an upper fastener attaching said elastic stretch band to said upper leg strap assembly;
a lower fastener attaching said elastic stretch band to said lower leg strap assembly;
said upper and lower leg strap assemblies being able to be formed into a circular shape by said user so that said upper leg strap assembly fits around said user's thigh and said lower leg strap assembly fits around said user's ankle;
said upper and lower leg strap assemblies being configured to releasably secure said exercising device to said user's leg;
said elastic stretch band being attached to both said upper leg strap assembly and said lower leg strap assembly with said stretch band extending from said upper leg strap assembly, over said portable front brace assembly and to said lower leg strap assembly so that a leg straightening pressure is placed on said knee joint;
said portable front brace assembly is comprised of an upper horizontal brace panel, a lower horizontal brace panel and a vertical brace panel that extends between and fixedly connects to said upper horizontal brace panel and said lower horizontal brace panel;
said upper and lower horizontal brace panels terminating at their free ends in said upper and lower padded portions, which padded portions conform with said user's leg so that said upper horizontal panel resides just above said user's knee and said lower horizontal panel resides just below said user's knee; and
said vertical brace panel including extending tabs on all four corners that act as guides for said elastic stretch band when said elastic stretch band is stretched over said vertical brace panel.

7. Knee rehabilitation exercise device as claimed in claim 6 wherein said elastic stretch band in conjunction with said portable front brace assembly provides passive stretching to said user's knee joint and surrounding muscles.

8. Knee rehabilitation exercise device as claimed in claim 6 wherein:
said upper fastener comprises a front facing upwardly turned L hook on the upper leg strap assembly and an aperture defined in said elastic stretch band, which aperture receives said front facing upwardly turned L hook to attach said elastic stretch band to said upper leg strap assembly; and
said lower fastener comprises a front facing downwardly turned L hook on the lower leg strap assembly and an aperture defined in said elastic stretch band, which aperture receives said front facing downwardly turned L hook to attach said elastic stretch band to said lower leg strap assembly.

9. A knee rehabilitation exercise device comprising:
a left leg brace;
a right leg brace;
an upper leg strap assembly;
a lower leg strap assembly; and
a portable brace assembly comprising an elastic member, a knee pad having a surface for engaging a user's leg, and a support member;
said left and right leg braces each comprised of a rigid upper member and a rigid lower member rotatably pinned together at the area of said user's knee joint;
said rigid upper member of each of said left and right leg braces being attached to said upper leg strap assembly;
said rigid lower member of each of said left and right leg braces being attached to said lower leg strap assembly;
said upper and lower leg strap assemblies being able to be formed into a circular shape by said user so that said upper leg strap assembly fits around said user's thigh and said lower leg strap assembly fits around said user's ankle;
said upper and lower leg strap assemblies being configured to releasably secure said exercising device to said user's leg;

said elastic member being attached to both said rigid upper and rigid lower members of both said left leg brace and said right leg brace; and said support member being centrally retained between said elastic member and said knee pad, wherein said knee pad and said support member can be installed on the front side of a said user's knee to allow said user to perform passive knee joint extension.

10. A knee rehabilitation exercise device comprising:

a left leg brace;

a right leg brace;

an upper leg strap assembly;

a lower leg strap assembly; and a portable brace assembly comprising an elastic member, a knee pad having a surface for engaging a user's leg, and a support member;

said left and right leg braces each comprised of a rigid upper member and a rigid lower member rotatably pinned together at the area of said user's knee joint;

said rigid upper member of each of said left and right leg braces being attached to said upper leg strap assembly;

said rigid lower member of each of said left and right leg braces being attached to said lower leg strap assembly;

said upper and lower leg strap assemblies being able to be formed into a circular shape by said user so that said upper leg strap assembly fits around said user's thigh and said lower leg strap assembly fits around said user's ankle;

said upper and lower leg strap assemblies being configured to releasably secure said exercising device to said user's leg;

said elastic member being attached to both said upper and lower members of both said left leg brace and said right leg brace;

said support member being centrally retained between said elastic member and said knee pad; and said knee pad and said support member can be installed on the rear side of said user's knee to allow said user to perform leg extension resistive exercise.

* * * * *